United States Patent [19]

Enomoto et al.

[11] 4,198,405

[45] Apr. 15, 1980

[54] PROSTAGLANDINE DERIVATIVES

[75] Inventors: Satoru Enomoto, Fujisawa; Kiro Asano; Humio Tamura, both of Kukizaki; Hiromitsu Tanaka, Tokyo, all of Japan

[73] Assignee: Kureha Kagaku Kogyo Kabushiki Kaisha, Tokyo, Japan

[21] Appl. No.: 1,269

[22] Filed: Jan. 5, 1979

[30] Foreign Application Priority Data

Jan. 31, 1978 [JP] Japan ................................ 53/9652
Aug. 29, 1978 [JP] Japan .............................. 53/104434

[51] Int. Cl.$^2$ ..................... C07J 51/00; A61K 31/56
[52] U.S. Cl. ............................... 424/242; 260/397.4; 260/397.5; 424/243
[58] Field of Search ................. 560/121; 260/397.4, 260/397.5; 424/242, 243

[56] References Cited

U.S. PATENT DOCUMENTS

| 3,732,261 | 5/1973 | Smythies | 260/397.4 |
| 3,839,409 | 10/1974 | Bergstrom et al. | 560/121 |

*Primary Examiner*—Robert Gerstl
*Attorney, Agent, or Firm*—Oblon, Fisher, Spivak, McClelland & Maier

[57] ABSTRACT

Prostaglandine derivatives are composed of a prostaglandine and a steriod hormone with or without a binding group.

The prostaglandine derivatives have extraordinarily reduced side-effect and superior physiological activity, particularly effect of abortion in comparison with those of prostaglandines.

11 Claims, 5 Drawing Figures

PROSTAGLANDINE DERIVATIVES

BACKGROUND OF THE INVENTION

The present invention relates to novel prostaglandine derivatives which reduce extraordinarily side-effect maintaining superior physiological activity and preparation thereof and usages thereof.

As it is well known, prostaglandines are found in human-body and are important physiological active compounds which impart hypotonia effect, gastric juice secretion inhibiting effect, bronchiectatic effect, blood platelet agglutination inhibiting effect or promoting effect.

Prostaglandines are abbreviated as PGs hereinafter. PGE and PGF are well known to have some special physiological activities such as hysterotrimus and yellow body degeneration, and they are useful for parturifacient, abortion at initial or middle stages of pregnancy and placental abruption after partus and control of menstrual disorder. (Brit. Med. J., 4,618(1968), Brit. Med. J., 4 621(1968), Amr. N.Y. Acad. Sci., 180,456(1970).

It is also possible to expect control of sexual cycle of female mammals, abortion and contraception.

However, the useful prostaglandines cause, in its administration as a medicine, nausea, vomitting and diarrhea and also sudden variations of blood pressure, pulse and respiration. In spite of the fact that prostaglandines have been expected as useful medicines, they have been limited to only for special therapy because of serious side-effect.

The inventors have studied to develop novel prostaglandine derivatives having extraordinarily reduced its side-effect.

SUMMARY OF THE INVENTION

It is an object of the present invention to provide novel prostaglandine derivatives which are useful for applications of prostaglandines in higher degree by reducing extraordinarily its side-effect.

It is another object of the present invention to provide a process for producing novel prostaglandine.

The novel prostaglandine derivatives are conjugates of prostaglandine-steroid hormone having hydroxyl, acetoxy propionyloxy benzoyloxy or oxo group at 3-position.

The conjugate of prostagradine-steroid hormone can be produced by reacting a prostaglandin or an acetylated prostaglandin with hydroxyl group at 17- or 21-position of a steroid hormone having hydroxyl, acetoxy, propionyloxy, benzoyloxy or oxo group at 3-position by their direct reaction or by binding with a binding agent selected from the group consisting of compounds having the formula $X(CH_2)_nCOOH$, $X(CH_2)_nCOX$,

$HOOC(CH_2)_nCOOH$,
and $XOC(CH_2)_nCOX$ wherein n is 1 or 2 and X is a halogen atom with or without an acetylation.

DETAILED DESCRIPTION OF THE PREFERRED EMBODIMENTS

The novel prostaglandine derivatives have the formula (I) or (I')

(I)

(I')

In the formula (I) or (I'), R is hydrogen atom or acetyl group; Z is —OR or =O; n is 1 or 2 and m is 0, 1 or 2.

In the formula (I), St is selected from the group consisting of the groups having the formula (II) to (IX)

(II)

(III)

(IV)

-continued

(V)

(VI)

(VII)

(VIII)

-continued

(IX)

wherein R' is selected from among hydrogen atom, acetyl group propionyl group and benzoyl group.

The typical prostaglandine derivatives (I) can be classified as follows.

unit $B_1$ unit $B_1'$ unit $B_1''$ unit $B_1'''$ unit $B_2$

Group I

| $A_1-B_1$ | $A_1'-B_1$ | $A_2-B_1$ | $A_2'-B_1$ | $A_3-B_1$ | $A_3'-B_1$ |
| $A_1-B_1'$ | $A_1'-B_1'$ | $A_2-B_1'$ | $A_2'-B_1'$ | $A_3-B_1'$ | $A_3'-B_1'$ |
| $A_1-B_1''$ | $A_1'-B_1''$ | $A_2-B_1''$ | $A_2'-B_1''$ | $A_3-B_1''$ | $A_3'-B_1''$ |
| $A_1-B_1'''$ | $A_1'-B_1'''$ | $A_2-B_1'''$ | $A_2'-B_1'''$ | $A_3-B_1'''$ | $A_3'-B_1'''$ |
| $A_1-B_2$ | $A_1'-B_2$ | $A_2-B_2$ | $A_2'-B_2$ | $A_3-B_2$ | $A_3'-B_2$ |

Group II $$A_1-O-(CH_2)_{\overline{n}}\overset{O}{\underset{\|}{C}}-B_1 \quad A_1'-O-(CH_2)_{\overline{n}}\overset{O}{\underset{\|}{C}}-B_1 \quad A_2-O-(CH_2)_{\overline{n}}\overset{O}{\underset{\|}{C}}-B_1 \quad A_2'-O-(CH_2)_{\overline{n}}\overset{O}{\underset{\|}{C}}-B_1$$

$$A_1-O-(CH_2)_{\overline{n}}\overset{O}{\underset{\|}{C}}-B_1' \quad A_1'-O-(CH_2)_{\overline{n}}\overset{O}{\underset{\|}{C}}-B_1' \quad A_2-O-(CH_2)_{\overline{n}}\overset{O}{\underset{\|}{C}}-B_1' \quad A_2'-O-(CH_2)_{\overline{n}}\overset{O}{\underset{\|}{C}}-B_1'$$

$$A_1-O-(CH_2)_{\overline{n}}\overset{O}{\underset{\|}{C}}-B_1'' \quad A_1'-O-(CH_2)_{\overline{n}}\overset{O}{\underset{\|}{C}}-B_1'' \quad A_2-O-(CH_2)_{\overline{n}}\overset{O}{\underset{\|}{C}}-B_1'' \quad A_2'-O-(CH_2)_{\overline{n}}\overset{O}{\underset{\|}{C}}-B_1''$$

$$A_1-O-(CH_2)_{\overline{n}}\overset{O}{\underset{\|}{C}}-B_1''' \quad A_1'-O-(CH_2)_{\overline{n}}\overset{O}{\underset{\|}{C}}-B_1''' \quad A_2-O-(CH_2)_{\overline{n}}\overset{O}{\underset{\|}{C}}-B_1''' \quad A_2'-O-(CH_2)_{\overline{n}}\overset{O}{\underset{\|}{C}}-B_1'''$$

$$A_1-O-(CH_2)_{\overline{n}}\overset{O}{\underset{\|}{C}}-B_2 \quad A_1'-O-(CH_2)_{\overline{n}}\overset{O}{\underset{\|}{C}}-B_2 \quad A_2-O-(CH_2)_{\overline{n}}\overset{O}{\underset{\|}{C}}-B_2 \quad A_2'-O-(CH_2)_{\overline{n}}\overset{O}{\underset{\|}{C}}-B_2$$

$$A_3-O-(CH_2)_{\overline{n}}\overset{O}{\underset{\|}{C}}-B_1 \quad A_3'-O-(CH_2)_{\overline{n}}\overset{O}{\underset{\|}{C}}-B_1$$

$$A_3-O-(CH_2)_{\overline{n}}\overset{O}{\underset{\|}{C}}-B_1' \quad A_3'-O-(CH_2)_{\overline{n}}\overset{O}{\underset{\|}{C}}-B_1'$$

$$A_3-O-(CH_2)_{\overline{n}}\overset{O}{\underset{\|}{C}}-B_1'' \quad A_3'-O-(CH_2)_{\overline{n}}\overset{O}{\underset{\|}{C}}-B_1''$$

$$A_3-O-(CH_2)_{\overline{n}}\overset{O}{\underset{\|}{C}}-B_1''' \quad A_3'-O-(CH_2)_{\overline{n}}\overset{O}{\underset{\|}{C}}-B_1'''$$

$$A_3-O-(CH_2)_{\overline{n}}\overset{O}{\underset{\|}{C}}-B_2 \quad A_3'-O-(CH_2)_{\overline{n}}\overset{O}{\underset{\|}{C}}-B_2 \;(n=1 \text{ or } 2)$$

The unit $B_1$ can be substituted with one of the following units.

(IV)

(V)

(VI)

(VII)

(VIII)

(IX)

wherein R' is selected from among hydrogen atom, acetyl group, propionyl group and benzoyl group.

The compounds in Group II are especially important.

Typical prostaglandine derivatives having the formula (I) include estra-1,3,5(10)-triene-3-hydroxy-17-oxycarbonylmethyl-9α, 11α, 15α-trihydroxy-5(cis)-13(trans)-prostadienoate (PGF$_2$αE) or (PGFE),estra-1,3,5(10)-triene-3-hydroxy-17-oxycarbonylethyl-9α, 11α, 15α-trihydroxy-5(cis)-13(trans)-prostadienoate, estra-1,3,5-(10)-triene-3-hydroxy-17-oxycarbonylmethyl-9α, 11α, 15α-triacetoxy-5(cis)-13(trans)-prostadienoate (PGFE-3AC); estra-1,3,5(10)-triene-3-hydroxy-17-oxycarbonylethyl-9α, 11α, 15α-triacetoxy-5(cis)-13-(trans)-prostadienoate; estra-1,3,5(10)-triene-3-acetoxy-17-oxycarbonylmethyl-9α, 11α, 15α-triacetoxy-5(cis)-13(trans)-prostadienoate (PGFE-4AC); and estra-1,3,5(10)-triene-3-acetoxy-17-oxycarbonylethyl-9α, 11α, 15α-triacetoxy-5-(cis)-13(trans)-prostadienoate.

The prostaglandine derivatives (I) can be produced by using 9α, 11α, 15α-trihydroxy-5(cis)-13(trans)-prostadienoic acid (hereinafter referring to PGF$_2$α) and estradiol as main starting materials.

However, when these prostaglandine derivatives (I) are administrated, the characteristic side-effects of PGF$_2$α are not found and pharmacological effects such as activity for stimulating hysterotrimus, abortion, yellow body degeneration and nidation inhibiting effect are greatly imparted. Accordingly, the novel prostaglandine derivatives (I) are extraordinarily effective for abortion, parturifacient, improvement for fertilization and estrus regulation contraception and menstruation facilitation.

The compounds of the present invention, the preparations thereof, the pharmacological tests, the formulation as medicines, the administration and the does will be illustrated.

The prostaglandine derivatives (I) can be produced as follows. In the present invention, PGE$_1$, PGE$_2$, PGE$_3$, PGF$_1\alpha$, PGF$_2\alpha$ and PGF$_3\alpha$ can be used as the prostaglandines (KAGAKU TO SEIBUTSU Vol. 15 No. 2 page 80 to 88; 1977).

Conjugates of prostaglandine-steroid hormone can be produced with the prostaglandine and the steroid hormone compound by their direct reaction or by using a suitable binding agent between them.

The binding agent can be a compound having the formula

X(CH$_2$)$_n$COOH (n is 1 or 2; and X is a halogen atom) such as $\alpha$-monochloroacetic acid, $\alpha$-monobromoacetic acid, and $\beta$-monobromopropionic acid; a compound having the formula X(CH$_2$)$_n$COX such as $\alpha$-monochloroacetyl chloride and $\alpha$-monobromoacetylbromide; a compound having the formula HOOC(CH$_2$)$_n$COOH or XOC(CH$_2$)$_n$COX such as malonic acid and succinic acid and acid dichloride thereof.

These binding agent can be used by the conventional chemical manner.

The prostaglandine derivatives (I) can be produced by reacting a steroid hormone such as estrone, estradiol, estriol or progesterone or a steroid hormone derivative having a conjugating group with 9$\alpha$, 11$\alpha$, 15$\alpha$-trihydroxy-5(cis)-13(trans)prostadienoic acid or a salt thereof.

The steroid hormone derivative having a binding group can be easily obtained by reacting a steroid hormone such as estradiol with the above-mentioned binding agent.

The binding agent should be reacted with OH group at 17 or 21 position of the selected steroid hormone.

The reaction of the steroid hormone such as estradiol with the binding agent is preferably carried out in a solvent such as anhydrous tetrahydrofuran preferably an aprotic solvent.

The reaction temperature is usually not so high and sometimes, room temperature or lower.

The prostaglandine is usually used in a form of a salt thereof especially a silver salt.

It is possible to acetylate the prostaglandine before reacting with the steroid hormone or its derivative.

The reaction of a metal salt of prostaglandine with the steroid hormone derivative can be carried out by mixing them in solvent such as DMSO in the dark.

In the acetylation, acetic anhydride is added in an inert solvent such as pyridine.

The reaction temperature can be about room temperature though it can be varied.

The resulting product can be purified by elution column chromatography on silica gel with some organic solvents.

Some examples for producing the prostaglandine derivatives (I) will be illustrated.

(1) PGFE can be produced as an oily matter by the reaction of BrCH$_2$COBr with OH group at 17 position of estradiol to obtain estra-1,3,5(10)-triene-3-ol-17-bromoacetate at the first reaction and then by the reaction of the above obtained product with a metal salt (Ag salt) of carboxyl group of PGF$_2\alpha$ in a solvent such as DMSO in the dark at the final reaction.

(2) PGFE-4AC can be produced as an oily matter by the reaction of BrCH$_2$COBr with OH group at 17-position of estradiol to obtain estra-1,3,5(10)-triene-3-ol-17-bromoacetate at the first reaction and by the reaction of the above obtained product with a metal salt (Ag salt) of carboxyl group of PGF$_2\alpha$ in a solvent such as DMSO in the dark at the second reaction and then, by the reaction of the separated second reaction product with acetic anhydride in solvent such as pyridine.

(3) PGFE-3Ac can be produced as an oily matter by the acetylation of PGF$_2\alpha$ with acetic anhydride in an inert solvent such as pyridine and converting acid part of the acetylated PGF$_2\alpha$ to a metal salt (silver salt) of the acetylated PGF$_2\alpha$ and then by the reaction of the obtained metal salt of the acetylated PGF$_2\alpha$ with estra-1,3,5(10)-triene-3-ol-17-bromoacetate.

(4) When estra-1,3,5(10)-triene-3-ol-17-bromopropionate is used instead of estra-1,3,5(10)-triene-3-ol-17- bromoacetate, the corresponding products can be obtained.

(5) The conjugate of $PGF_2\alpha$ and estradiol can be produced by brominating OH group at 17-position of estradiol with $PBr_5$ in an inert solvent such as tetrahydrofuran and reacting the product with a metal salt (silver salt) of prostaglandin in an inert solvent such as DMSO. Other derivatives can be produced by the same method.

The structures of these products are confirmed by IR spectrum, elementary analysis and NMR.

The side-effects of these products will be illustrated.

Acute toxicities ($LD_{50}$) of PGFE,PGFE-4AC and PGFE-3A are measured by intravenous injections at a dose of 400 mg/kg to ten of ICR-JCL female mice (4 weeks age).

All of mice (10) are survived. From the viewpoint of the fact that $LD_{50}$ of $PGF_2\alpha$ is 56 mg/kg, it is clear the PGFE, PGFE-4AC and PGFE-3A are significantly safe.

The tachycardia, respirogram and electrocardiogram of mice in pregnancy before and after the administration of $PGF_2\alpha$, PGFE, PGFE-4AC and PGFE-3AC are tested by a biophysiograph 180-4(4ch) (manufactured by San-ei Sokuki K.K.).

As the results, in contrast to the fact that abnormal conditions are clearly observed in the administration of $PGF_2\alpha$, any abnormal condition is not observed in case of PGFE,PGFE-4Ac, or PGFE-3AC.

According to these side effect tests, it is found that PGFE, PGFE-4AC and PGFE-3AC have sufficiently low toxicities and reduced side-effects.

The efficiency of abortion of PGFE,PGFE-4AC and PGFE-3AC are tested as pharmacological effects in suitable administrations and doses by using ICR-JCL pregnant mice.

As the results, PGFE, PGFE-4AC and PGFE-3AC impart greatly superior effect in comparison with that of $PGF_2\alpha$.

The abortion is incomplete in the continuous administration of $PGF_2\alpha$ at dose of 15$\alpha$ (4.24×10$^{-8}$ moles)-/mouse during 4 days, but the satisfied results are obtained in case of PGFE, PGFE-4AC or PGFE-3AC at the same dose or less than that.

The hydroxyl groups at 9, 11 and 15-positions of $PGF_2\alpha$ are active sites, and when the hydroxyl groups are acetylated, it is usually considered to be inactive.

In PGFE-4AC and PGFE-3AC, the hydroxyl groups are acetylated, however, they have surprisingly significant superior effect.

The prostaglandine derivatives (I) of the present invention can be formulated in desirable forms for injection, oral administration, intravagina administration or coating. For example, they are formulated in forms of solid compositions such as table pill, powder, granules and capsule and liquid compositions such as sirup for the oral administration. For example, in the case of the solid compositions, starch, calcium carbonate and lactose can be incorporated as the vehicle and a lubricant can be also incorporated together with the product of the present invention. In the case of the liquid composition for oral administration, the product of the present invention is mixed with pharmacologically acceptable vehicle such as emulsifier, suspending agent and additive for sirup, water, alcohol, liquid paraffin and oil of olive, and also sweetening and flavour. It is possible to form a capsule by using gelatin.

In the case of the solid compositions for intravaginal administration, the product of the present invention can be mixed with wax higher fatty acid or higher alcohol which has a suitable melting point for melt in vagina and if necessary, a disintegrator having suitable viscosity.

In the case of injection, the product of the present invention is dissolved in water and if necessary, a suitable additive such as ethanol, surfactants, emulsifiers, saline stabilizers, pH regulators and nutrients.

The concentration of the product of the present invention in the formulation is preferably higher than 0.0025 wt.% for injections; and higher than 0.1 wt.% for oral compositions.

The dose of the product of the present invention is 0.1 $\mu$g to 500 $\mu$g/day/pregnant woman preferably 0.001 to 50 mg/day/pregnant woman and also a suitable dose can be determined by administrative method and condition of pregnancy.

Some examples will be described for the purpose of illustration only.

EXAMPLE 1

Preparation of estra-1,3,5(10)-triene-3-hydroxy-17-oxycarbonylmethyl-9$\alpha$,11$\alpha$,15$\alpha$-trihydroxy-5(cis)-13(trans)prostadienoate (PGFE) and potassium or silver salt of 9$\alpha$,11$\alpha$,15$\alpha$-trihydroxy-5(cis)-13(trans)-prostadienoic acid ($PGF_2\alpha$)

(a) Preparation of potassium salt of $PGF_2\alpha$

1 Ml of water was added to 0.1053 g (2.97×10$^{-4}$ mole) of $PGF_2\alpha$ and the mixture was stirred at +1° to −2° C. and 1 ml of aqueous solution containing 0.0205 g of KOH was slowly added to the mixture. The slurry became a clear solution at stirring of about one hour and the pH was in the range of 7.5 to 8.5.

(b) Preparation of silver salt of $PGF_2\alpha$ 0.05301 Gram of $AgNO_3$ was dissolved in a small amount of water and the solution was added to the aqueous solution of the potassium salt of $PGF_2\alpha$ in the dark. The solution was stirred for about 15 minutes to precipitate a white silver salt of $PGF_2\alpha$. After filtration of the white precipitate, the collected precipitate was washed with water and then, with ether. Then, 0.1085 g of a white silver salt was obtained by drying at room temperature under a reduced pressure. (Yield: 79.14%)

Preparation of estra-1,3,5(10)-triene-3$\beta$-ol-17$\beta$-bromoacetate

10 Gram of estradiol was dissolved in 400 ml of anhydrous tetrahydrofurans(THF) and then, 8.8 g of anhydrous pyridine was added.

A solution containing 74 g of carbon tetrachloride in 22.5 g of $\alpha$-bromoacetyl bromide was dropwisely added to a solution of estradiol at −5° to −7° C. The mixture was kept for one night to continue the reaction. After the reaction, the precipitate was filtered and the solvent was distilled off from the filtrate.

The residue was dissolved in ether and recrystallized to obtain estra-1,3,5(10)-triene-3,17$\beta$-dibromoacetate. Then, 2 g of the product was dissolved in 900 ml of methaol and cooled to −5° C. and 20 ml of an aqueous solution containing 0.2 g of $K_2CO_3$ was dropwisely added.

After 30 minutes, 1,000 ml of water was added to the solution and the resulting precipitate was separated and dried. It was confirmed that the product is estra-1,3,5(10)-triene-3β-ol-17β-bromoacetate by an elementary analysis and IR spectrum.

Reaction of silver salt of $PGF_2\alpha$ with estra-1,3,5(10)-triene-3β-ol-17β-bromoacetate 0.1085 Gram ($2.35 \times 10^{-4}$ mole) of silver salt of $PGF_2\alpha$ was dissolved in 2 cc of dimethylsulfoxide (DMSO) in the dark, and then, 0.1000 g of estra-1,3,5(10)-3β-ol-17β-bromoacetate was added and the mixture was stirred at room temperature for 2 days. The precipitated silver bromide was removed and the remaining solution became an emulsion at the cooled state by adding 20 ml of water. A pale yellow oily product was obtained from the emulsion by a centrifugal separation.

The reaction product was chromatographed on 42 g of silica gel with a mixed solvent (cyclohexane, ethyl acetate and ethanol at ratios of 45:45:10 by volume) to obtain a purified matter at a yield of 68.95%. It was confirmed that the product was a conjugate of $PGF_2\alpha$ and estradiol having the following formula.

Conjugate of $PGF_2\alpha$ and estradiol.

Elementary Analysis:

|  | C | H |
| --- | --- | --- |
| Calculated (%) | 72.07 | 8.71 |
| Found (%) | 71.60 | 8.00 |

IR spectrum: (cm$^{-1}$) 3400, 2920, 2850, 1735, 1610, 1580, 1495, 1440, 1378, 1350, 1280, 1215, 1140, 1075, 1040, 1020, 1000, 960, 920, 915, 865, 810 780, 720.

EXAMPLE 2

Preparation of conjugate of $PGF_2\alpha$ and estradiol

1 Gram of estradiol was dissolved in 65 ml of tetrahydrofuran containing 5 g of $CaCO_3$ and 5.0 g of $PBr_5$ was added during 30 minutes under stirring at −4° C. and the mixture was further stirred for 30 minutes at −4° C. and then, the stirring continued for 20 minutes at 0° C. and 3.5 hours at 20° C. to react it. The reaction mixture was poured in an aqueous solution of $NaHCO_3$ (at 0° C.). The product was extracted with ether and purified with acetone (0.7 g of purified product).

The purified product (bromide) was reacted with $PGF_2\alpha$-Ag prepared in Example 1, to obtain the following conjugate.

IR spectrum: (cm$^{-1}$) 3400, 2920, 2850, 1735, 1600, 1570, 1500, 1440, 1378, 1350, 1280, 1215, 1140, 1080, 1040, 1020, 1000, 955, 918, 910, 870, 810, 780, 712.

The physiological activity was measured in accordance with the method of Example 1 except using the resulting conjugate. As the result, it was confirmed that the conjugate was bonded to the estrogen receptor to cause hysterotrimus.

EXAMPLE 3

Conjugate of $PGE_2$ and progesterone 3.3 Gram of 11-desoxycorticosterone as a progesterone derivative was dissolved in a mixed solvent of 200 ml of anhydrous THF and 10 ml of anhydrous pyridine and the solution was kept at −5° to −7° C.

A solution of 0.3 g of α-bromoacetylbromide in 80 g of $CCl_4$ was dropwisely added to the solution of 11-desoxycorticosterone. The mixture was stirred and kept at room temperature for one night.

After the reaction, the precipitate was filtered and the solvent was distilled off from the filtrate and a residue was recrystallized from ether.

In IR spectrum, the absorption based on OH group at 21-position was not found and the characteristic absorption of ester bond was found at 1735 cm$^{-1}$. From the results of IR spectrum and an elementary analysis, it was confirmed that α-bromoacetyl group was introduced into OH group at 21-position of 11-desoxycorticosterone.

The resulting compound was reacted with $PGE_2$-Ag prepared in Example 1 to obtain the conjugate of $PGE_2$ and progesterone ($PGE_2P$).

In UV absorption spectrum, the characteristic absorption of conjugated carbonyl group at 241 nm was found.

The physiological activity was measured in accordance with the method of Example 1 except using the resulting conjugate. As the result, it was confirmed that the conjugate was bonded to the estrogen receptor to cause hysterotrimus.

EXAMPLE 4

Preparation of estra-1,3,5(10)-triene-3-acetoxy-17-oxycarbonylmethyl-9α,11α,15α-triacetoxy-5(cis)-13(trans)prostadienoate The potassium salt and silver salt of PGF$_2$α and estra-1,3,5(10)-triene-3-ol-17-bromoacetate were prepared by the process of Example 1 and the reaction of silver salt of PGF$_2$α with estra-1,3,5(10)-triene-3-ol-17-bromoacetate was carried out by the process of Example 1.

Acetylation of conjugate of PGF$_2$α and estradiol

In a 10 ml conical flask, 0.0290 g of the conjugate of PGF$_2$α and estradiol (PGFE) was charged and 0.5 ml of anhydrous pyridine was added to dissolve it and then, 0.15 ml of acetic anhydride was added and the mixture was stirred at room temperature for one night. After the reaction, the solvent was removed at 45° C. under a reduced pressure to obtain 0.0351 g of acetylated conjugate of PGF$_2$α and estradiol (PGFE-4AC) which was an oily product.

It was confirmed that the product has the following structure by means of the elementary analysis and IR spectrum.

(PGFE-4AC)

Elementary Analysis:

|  | C | H |
| --- | --- | --- |
| Calculated (%) | 69.06 | 7.91 |
| Found (%) | 68.8 | 8.0 |

IR spectrum: (cm$^{-1}$) 2920, 2850, 1735, 1610, 1593, 1580, 1490, 1430, 1375, 1230, 1150, 1010, 960, 890, 865, 820, 793, 780, 750, 705, 676.

EXAMPLE 5

Preparation of estra-1,3,5(10)-triene-3-hydroxy-17-oxycarbonylmethyl-9α,11α,15α-triacetoxy-5(cis)-13(trans)-prostadienoate In 1.0 ml of anhydrous pyridine, 0.1008 g of PGF$_2$α was dissolved and then, 0.3 ml of acetic anhydride was added and the mixture was kept for one night. After the reaction, pyridine and acetic anhydride were removed at 40° C. under a reduced pressure and a residue was washed with water and the oily product was separated. Then, 2 ml of water and 3 ml of ethanol were added and then, 0.0186 g of potassium hydroxide was added to react it under cooling with water for 1 hour. A silver nitrate solution (AgNO$_3$ 0.0515 g) prepared by dissolving in 2 ml of water, was added to the reaction mixture to react it further for 1 hour in the dark to obtain 0.1140 g of silver salt of acetylated PGF$_2$α.

In 2 ml of DMSO, 0.11 g of silver salt of acetylated PGF$_2$α was dissolved and then, 0.10 g of estra-1,3,5(10)-3-ol-17-bromoacetate was added to react it for 48 hours in the dark. After the reaction, AgBr was removed by filtering through the G-4 filter. The filtrate was admixed with 20 ml of cold water and the resulting oily product was separated by a centrifugal separator. The product was chromatographed on 42 g of silica gel with a mixed solvent (cyclohexane, ethyl acetate and ethanol at ratios at 45:45:10 by volume). The purified product was oily.

It was confirmed that the product has the following structure by means of the elementary analysis and IR spectrum.

(PGFE-3AC)

Elementary Analysis:

|  | C | H |
| --- | --- | --- |
| Calculated (%) | 69.70 | 8.08 |
| Found (%) | 68.90 | 8.0 |

IR spectrum: (cm$^{-1}$) 3400, 2920, 2850, 1735, 1610, 1580, 1500, 1440, 1370, 1230, 1145, 1080, 1020, 960, 915, 865, 812, 790, 780, 725.

EXAMPLE 6

0.1 Gram (2.17×10$^{-4}$ mole) of PGF$_2$α.Ag salt was dissolved in 1 ml of anhydrous DMSO and 0.13 g (2.60×10$^{-4}$ mole) of 3-benzoyloxy-1,3,5(10)-triene-17-β-monobromoacetate was added in the dark to react it at room temperature.

After the reaction, AgBr was separated and the filtrate was cooled and admixed with water and the product was separated as oily material at the bottom by a centrifugal separation.

The oily product was dried in vacuum in a desiccator and was dissolved in a mixed solvent of ethyl acetate, cyclohexane and ethanol (45:45:10 by volume) and the solution was passed through a silica gel column to obtain 0.12 g of PGFE-BA (yield 71.8%).

PGFE-BA

C$_{47}$H$_{62}$O$_9$
molecular weight 770

Elementary Analysis:

|  | C | H |
| --- | --- | --- |
| Calculated (%) | 73.25 | 8.05 |
| Found (%) | 73.01 | 7.98 |

IR spectrum: (cm$^{-1}$) 3400, 2920, 2840, 1735, 1600, 1580, 1490, 1450, 1418, 1380, 1350, 1260, 1208, 1170, 1145, 1078, 1060, 1020, 1000, 960, 910, 890, 874, 812, 796, 780, 698, 680, 610.

EXAMPLE 7

21.0 Milligram ($2.73 \times 10^{-5}$ mole) of PGFE-BA was dissolved in 0.5 ml of anhydrous pyridine and 0.15 ml of acetic anhydride was added and the mixture was cooled with ice to react them and the reaction mixture was kept in one night. After the reaction, the solvent was distilled off in vacuum at 40° C. and the residue was dissolved in a mixed solvent of ethyl acetate and cyclohexane (50:30 by volume) and the solution was passed through a silica gel column to obtain 23.5 mg of PGFE-3AC-BA (yield 96.31%).

PGFE-3AC-BA

Elementary Analysis:

|  | C | H |
|---|---|---|
| Calculated (%) | 71.0 | 7.59 |
| Found (%) | 71.2 | 7.62 |

IR spectrum: (cm$^{-1}$) 2920, 2850, 1735, 1600, 1580, 1490, 1450, 1425, 1370, 1240, 1170, 1145, 1078, 1060, 965, 915, 890, 705, 680.

EXAMPLE 8

0.1 Gram ($2.17 \times 10^{-4}$ mole) of PGF$_2\alpha$-Ag salt was dissolved in 1 ml of anhydrous DMSO and then 0.114 g ($2.6 \times 10^{-4}$ mole) of 3-propionyl-oxy-1,3,5(10)-triene-17-$\beta$-monobromoacetate was added in the dark to react it at room temperature for 3 days. After the reaction, AgBr was separated and the filtrate was admixed with water and the product was separated as oily material at room temperature by a centrifugal separation.

The oily product was dissolved in a mixed solvent of ethyl acetate, cyclohexane and ethanol (45:45:10 by volume) and the solution was passed through a silica gel column to obtain 0.12 g of an oily product which was confirmed to be the object compound of PGFE-PR by the elementary analysis and IR spectrum.

PGFE-PR molecular weight 722

Elementary Analysis:

|  | C | H |
|---|---|---|
| Calculated (%) | 71.47 | 8.59 |
| Found (%) | 71.30 | 8.55 |

IR spectrum: (cm$^{-1}$) 3400, 2920, 2840, 1735, 1600, 1590, 1580, 1490, 1430, 1373, 1230, 1150, 1010, 960, 890, 820, 793, 780, 750.

EXAMPLE 9

0.145 Gram ($2.60 \times 10^{-4}$ mole) of 11-deoxy corticosterone-21-bromoacetate and 0.1 g ($2.17 \times 10^{-4}$ mole) of PGF$_2\alpha$.Ag salt were reacted in 1 ml of anhydrous DMSO in the dark for 3 days to obtain 1.3 g of an oily product which was confirmed to be the object compound of PGF-P by the elementary analysis and IR spectrum.

PGFP

$C_{43}H_{64}O_9$
molecular weight 724

Elementary Analysis:

|  | C | H |
|---|---|---|
| Calculated (%) | 71.27 | 8.84 |
| Found (%) | 71.50 | 8.62 |

IR spectrum: (cm$^{-1}$) 3420, 2950, 2920, 2850, 1750, 1725, 1665, 1612, 1450, 1420, 1385, 1320, 1270, 1230, 1190, 1145, 1080, 1050, 965, 940, 910, 860, 780, 760, 720, 680.

In accordance with the process of Example 7 except using PGF-P as the starting material, a partial acetylation was carried out to obtain an oily product which was confirmed to be the object compound of PGF-P-3AC by the elementary analysis and IR spectrum.

PGFP-3AC

Elementary Analysis:

|  | C | H |
|---|---|---|
| Calculated (%) | 68.77 | 8.77 |
| Found (%) | 69.00 | 8.52 |

IR spectrum: (cm$^{-1}$) 3000, 2950, 2920, 1750, 1735, 1705, 1610, 1580, 1430, 1405, 1385, 1368, 1320, 1270, 1230, 1190, 1145, 1080, 1050, 965, 940, 910, 860, 780, 760, 720, 680.

EXAMPLE 10

0.1 Gram (2.17×10⁻⁴ mole) of PGE₂Ag salt was dissolved in 1 ml of anhydrous DMSO and then, 0.13 g of 3-benzoyl-oxy-1,3,5(10)-triene-17-β-monobromoacetate was added in the dark to react it at room temperature for 3 days. After the reaction, the product was purified to obtain 0.12 g of colorless oily product which was confirmed to be the object compound of PGE₂E-BA by the elementary analysis and IR spectrum.

PGE₂E-BA

$C_{47}H_{61}O_9$
molecular weight 768

Elementary Analysis:

|  | C | H |
|---|---|---|
| Calculated (%) | 73.43 | 7,81 |
| Found (%) | 73.12 | 7.89 |

IR spectrum: (cm⁻¹) 3420, 3000, 2950, 2920, 2850, 1735, 1705, 1585, 1490, 1450, 1418, 1380, 1368, 1350, 1235, 1145, 1090, 1018, 965 890, 780, 720, 700, 680.

In accordance with the process of Example 7 except using PGE₂E-BA as the starting material, a partial acetylation was carried out at room temperature to obtain an oily product which was confirmed to be the object compound of PGE₂E-2AC-BA by the elementary analysis and IR spectrum.

PGE₂E-2AC-BA $C_{51}H_{64}O_{11}$
molecular weight 852

Elementary Analysis:

|  | C | H |
|---|---|---|
| Calculated (%) | 71.83 | 7.51 |
| Found (%) | 72.03 | 7.59 |

IR spectrum: (cm⁻¹) 2950, 2920, 2850, 1735, 1705, 1583, 1490, 1448, 1415, 1381, 1368, 1350, 1235, 1143, 1090, 1020, 970, 890, 780, 720, 698, 680.

EXAMPLE 11

0.1 Gram of PGE₁Ag salt was dissolved in 1 ml of anhydrous DMSO and then, 0.13 g of 3-benzoyl-oxy-1,3,5(10)-triene-17-β-monobromoacetate was added in the dark to react it at room temperature for 3 days. After the reaction, the product was purified to obtain 0.12 g of colorless product which was confirmed to be the object compound of PGE₁E-BA by the elementary analysis and IR spectrum.

$C_{47}H_{62}O_9$
molecular weight 770

Elementary Analysis:

|  | C | H |
|---|---|---|
| Calculated (%) | 73.24 | 8.05 |
| Found (%) | 73.12 | 7.89 |

IR spectrum: (cm⁻¹) 3420, 3000, 2950, 2920, 2850, 1735, 1705, 1585, 1490, 1450, 1418, 1380, 1368, 1350, 1235, 1145, 1090, 1018, 965, 890, 780, 720, 700, 680.

In accordance with the process of Example 7 except using PGE₁E-BA as the starting material, a partial acetylation was carried out at room temperature to obtain an oily product which was confirmed to be the object compound of PGE₁E-2AC-BA by the elementary analysis and IR spectrum.

PGE₁E-2AC-BA $C_{51}H_{66}O_{11}$
molecular weight 854

Elementary Analysis:

|  | C | H |
|---|---|---|
| Calculated (%) | 71.66 | 7.73 |
| Found (%) | 72.03 | 7.59 |

IR spectrum: (cm⁻¹) 2950, 2920, 2850, 1735, 1705, 1583, 1490, 1448, 1415, 1381, 1368, 1350, 1235, 1143, 1090, 1020, 970, 890, 780, 720, 698, 680.

Measurement of Physiological Activities of PGFE

Figure 1:
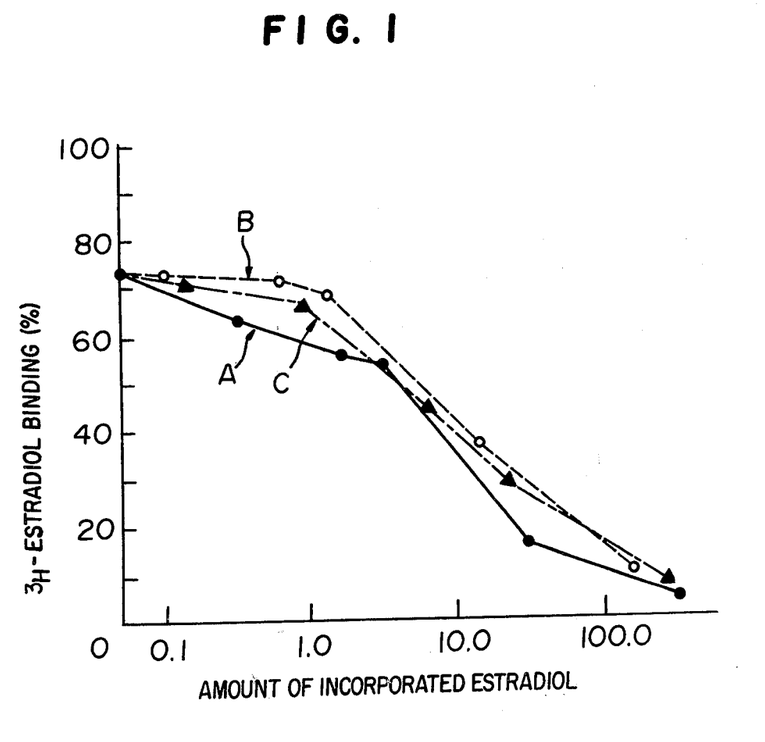

Binding function of estradiol and the PGFE to each uterus of rabbit were measured by the competitive receptor assay. Estradiol labelled by tritium (³H) was incubated with uterus of rabbit to bind it and then, estradiol or the PGFE was added to the system to measure the amount of free ³H-estradiol which was replaced by the added estradiol or the PGFE. The results are shown in FIG. 1. As it is clear from FIG. 1, it was found that the PGFE has the binding function to estrogen receptor as the same with the estradiol itself.

Hysterotrimus of the drugs were observed by the same operation applied to the oxytocin. 5γ of PGF₂α or 5 L to 50γ of the PGFE gaved of the hysterotrimus by intravenous injection to rats. In the former case, cardiac stop was caused whereas in the latter case, the cardiac activity was in the normal condition even though 50γ of the conjugate is administered whereby no side-effect was found.

The PGFE showed some delay in the beginning of hystrotrimus in comparison with $PGF_2\alpha$ itself. This fact indicates that the PGFE absorbed selectively in the uterus is hydrolysed to free $PGF_2\alpha$.

The abortion was studied with ICR-JCL pregnant mice by the continuous administration of the drug during 4 days and the side-effect in the administration was also examined.

After 0.2 ml of 50% ethanol-saline solution containing the PGFE at dose 10γ and 30γ/mouse or $PGF_2\alpha$ at dose 15γ/mouse (equimole of PGFE 30γ) was intravenously injected to the mice once a day during 4 days, their breedings were continued to confirm the abortion of the group administrated with the drugs until the partus of the control group administrated with only ethanol saline solution.

The results are as follows.

Table 1

| | Sample | Dose (γ/mouse) | Result of parturition (5 mice in group) | Effect of abortion (%) |
|---|---|---|---|---|
| Control | 50% ethanol - saline | 0 | 5 | 0 |
| Reference | $PGF_2\alpha$ solution | 15 | 5 | 0 |
| Invention | PGFE solution | 10 | 0 | 100 |
| | | 30 | 0 | 100 |

Efficiency of abortion =
$$\frac{\text{No. of pregnant mice} - \text{No. of delivered mice}}{\text{No. of pregnant mice}} \times 100$$

Side-effect Test of PGFE-3AC and PGFE-4AC

Acute toxicity ($LD_{50}$) and abnormal tachycardia, respirogram and electrocardiogram by a biophysiograph were tested.

In the measurement of $LD_{50}$, 10ICR-JCL female mice (4 week age) were used as one group. 0.2 ml of 50% ethanol-saline solution containing the drug of this invention was intravenously injected to the mice at several doses during 7 days to obtain their value of $LD_{50}$ by Litchfield-Wilcoxon graph method.

As the results, all of the mice were survived and any abnormality was not observed even in the administration of 400 mg/kg of PGFE-3AC or PGFE-4AC which is about 7 times of the $LD_{50}$ of $PGF_2\alpha$ (56 mg/kg). Accordingly, their $LD_{50}$ were too high to be impossible to measure directly. The fact shows that the products of PGFE-3AC and PGFE-4AC had remarkably low toxicity.

Electrocardiogram was measured by a biophysiograph 180-4 (4 ch) (manufactured by San-ei Sokuki K.K.) for ICR-JCL pregnant mice (6th day) at 3 minutes after the administration of each sample.

In the test, 0.2 ml of 50% ethanol-saline solution was intravenously injected to the mice at a dose of 30γ per mouse. As the reference, the $PGF_2\alpha$ was also used as the sample (a dose of 15γ per mouse).

The results of the measurements are shown in FIGS. 2 to 5 wherein mV is given on ordinate and time (second) is given on absciссas and the chart speed was 250 mm/sec.

Figure 2:
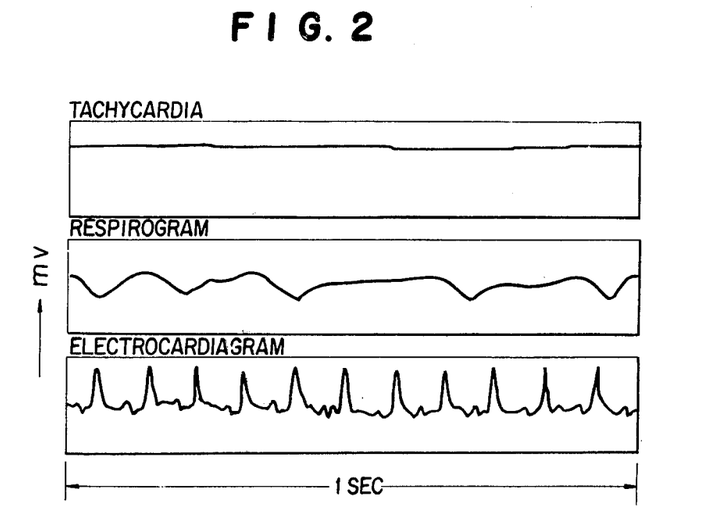

FIG. 2 shows the tachycardia, respirogram and electrocardiogram in the case of the intravenous injection of 0.2 ml of 50% ethanol saline solution.

Figure 3:
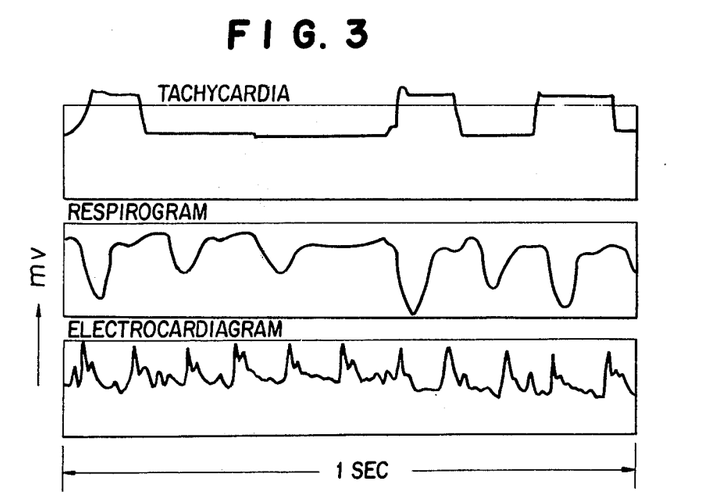

FIG. 3 shows the tachycardia, respirogram and electrocardiogram in the case of the intravenous injection of 0.2 ml of 50% ethanol saline solution containing $PGF_2\alpha$ at a dose of 15γ/mouse.

Figure 4:
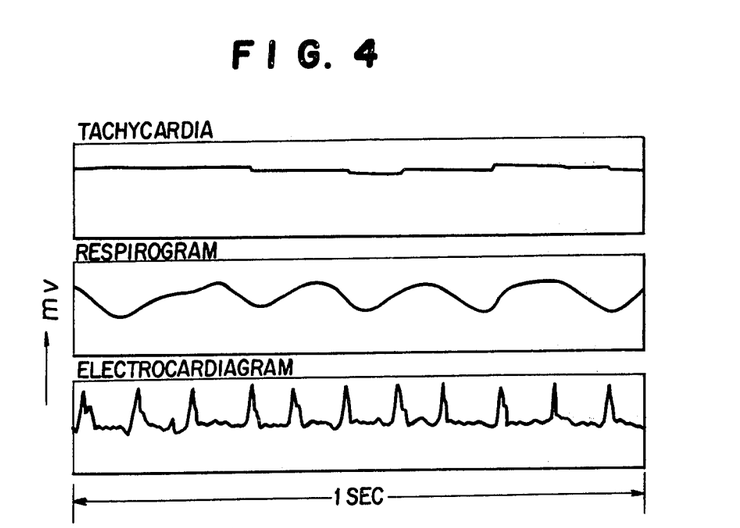

FIG. 4 shows the tachycardia, respirogram and electrocardiogram in the case of the intravenous injection of 0.2 ml of 50% ethanol saline solution containing PGFE-4AC at a dose of 30γ/mouse.

Figure 5:
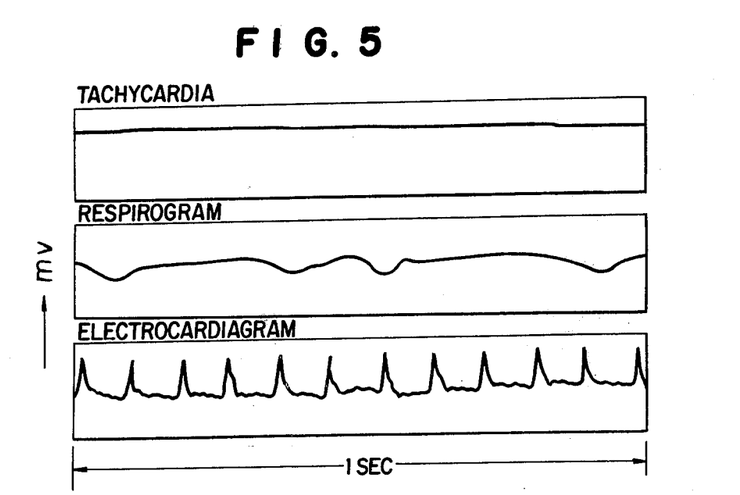

FIG. 5 shows the tachycardia, respirogram and electrocardiogram in the case of the intravenous injection of 0.2 ml of 50% ethanol saline solution containing PGFE-3AC at a dose of 30γ/mouse.

It is clear from the results of the measurement, the tachycardia, the respirogram and electrocardiagram after the administration of $PGF_2\alpha$ (FIG. 3) are abnormally different from those of the control (FIG. 2). However, the tachycardia, respirogram and electrocardiagram after the administration of PGFE-3AC or PGFE-4AC (FIGS. 4 and 5) are substantially the same with those of the control. Accordingly, PGFE-3AC and PGFE-4AC are advantageous medicines since they do not cause any abnormal symptom. The other prostaglandine derivatives of the present invention showed also the same effects.

Test of abortion of PGFE-3AC and PGFE-4AC

The continuous administrations were applied to ICR-JCL mice of the sixth day of pregnancy (5 mice as one group) to examine the efficiency of the abortion obtained by the drugs of this invention in comparison with that of $PGF_2\alpha$. After 0.2 ml of 5% ethanol-saline solution containing the PGFE-3AC, the PGFE-4AC or $PGF_2\alpha$ was given to the mice once a day during 4 days by intravenous injection and subcutaneous injection at some dose, their breeding were continued to confirm the abortion of the group administrated with the drugs until the partus of the control group administrated with only ethanol saline solution.

The results are shown in Tables. As it is clear from the test results, the efficiency of abortion of PGFE-4AC and PGFE-3AC are remarkably superior to that of the known compound $PGF_2\alpha$.

Table 2

| Test of abortion by subcutaneous injection: | | | |
|---|---|---|---|
| Sample | Dose (τ/mouse) | Result of parturition (5 mice in group) | Efficiency of abortion (%) |
| Control 5% Ethanol-saline sol. | 0 | 5 | 0 |
| Reference $PGF_2\alpha$ | 15 | 5 | 0 |
| $PGF_2\alpha$ | 30 | 4 | 20 |
| PGFE-4AC | 15 | 0 | 100 |
| Invention PGFE-4AC | 30 | 0 | 100 |
| PGFE-3AC | 15 | 0 | 100 |

Table 3

| Test of abortion by intravenous injection: | | | |
|---|---|---|---|
| Sample | Dose (τ/mouse) | Result of parturition (5 mice in group) | Efficiency of abortion (%) |
| Control 5% Ethanol-saline sol. | 0 | 5 | 0 |

Table 3-continued

Test of abortion by intravenous injection:

| Sample | Dose (γ/mouse) | Result of parturition (5 mice in group) | Efficiency of abortion (%) |
|---|---|---|---|
| | PGF$_2\alpha$ | 2.5 | 5 | 0 |
| Reference | PGF$_2\alpha$ | 5.0 | 5 | 0 |
| | PGF$_2\alpha$ | 15.0 | 4 | 20 |
| | PGFE-4AC | 2.5 | 3 | 40 |
| | PGFE-4AC | 5.0 | 0 | 100 |
| Invention | PGFE-3AC | 1.0 | 4 | 20 |
| | PGFE-3AC | 2.5 | 2 | 60 |
| | PGFE-3AC | 5.0 | 0 | 100 |

Test of abortion of other prostaglandine derivatives of the present invention.

The drugs of this invention were dissolved into oil of olive at several concentrations to obtain their effective doses of abortion (100% efficiency). 0.2 ml of the solution was subcutaneously injected to ICR-JCL pregnant mice (5 mice as one group).

After a single subcutaneous injection of 0.2 ml solution was applied to ICR-JCL pregnant mice at 4th day, their breedings were continued to confirm their abortions of the groups administered with the drugs until the partus of the control group administered only with the oil.

EXAMPLE 12

Table 4

Test of abortion by 1 shot subcutaneous injection

| | Sample | Dose mol/mouse | Result of parturition | Effect of abortion (%) |
|---|---|---|---|---|
| Control | olive oil | 0 | 5 | 0 |
| Reference | PGE$_2$ | 8.5 × 10$^{-8}$mol | 5 | 0 |
| | PGF$_2\alpha$ | 8.5 × 10$^{-8}$mol | 5 | 0 |
| | PGFE-BA | 5.6 × 10$^{-8}$mol | 1 | 80 |
| | PGFE-3AC-BA | 5.6× 10$^{-8}$mol | 0 | 100 |
| Invention | PGFE-Pr | 5.6 × 10$^{-8}$mol | 1 | 80 |
| | PGFP | 8.5 × 10$^{-8}$mol | 1 | 80 |
| | PGFP-3AC | 8.5 × 10$^{-8}$mol | 0 | 100 |
| | PGE$_2$E-BA | 5.6 × 10$^{-8}$mol | 1 | 80 |
| | PGE$_2$E-2AC-BA | 5.6× 10$^{-8}$mol | 0 | 100 |
| | PGE$_1$E-BA | 5.6 × 10$^{-8}$mol | 1 | 80 |
| | PEG$_1$E-2AC-BA | 5.6 × 10$^{-8}$mol | 0 | 100 |

Composition

| Formula 1 | | |
|---|---|---|
| PGFE-4AC | 0.05 | wt. parts |
| Nonionic surfactant | 2.0 | wt. parts |
| Ethanol | 30 | wt. parts |
| Physiological NaCl solution | 95 | wt. parts |

The components were heated and mixed and sterilized to prepare an injection.

| Formula 2 | | |
|---|---|---|
| PGFE-3AC | 0.5 | wt. parts |
| Mannitol | 35 | wt. parts |
| Carboxymethyl cellulose | 5 | wt. parts |
| Magnesium stearate | 5 | wt. parts |
| Sorbitol | 25 | wt. parts |
| Talc | 30 | wt. parts |

The components were mixed and pulverized and compressed to form a tablet having a diameter of 10 mm.

| Formula 3 | |
|---|---|
| PGFE-3AC | 0.02 g |
| Sodium phosphate | 6 g |
| Benzyl alcohol | 0.9 ml |
| Water | 100 ml |

The components were mixed and sterilized to prepare an injection.

What is claimed is:
1. Prostaglandin derivatives having the formula (I) or (I')

wherein, R is hydrogen atom or acetyl group; Z is —OR or =O; n is 1 or 2 and m is 0, 1 or 2, and St is selected from the group consisting of the groups having the formula (II) to (IX)

-continued

(IV)

(V)

(VI)

(VII)

-continued (VIII)

(IX)

wherein R' is selected from among hydrogen atom, acetyl group, propionyl group and benzoyl group.

2. Prostaglandin derivatives having the formula (X)

wherein n is 1 or 2 and m is 0, 1 or 2.

3. Prostaglandin derivatives having the formula (XI)

wherein R' is hydrogen atom, acetyl group, propionyl group and benzoyl group and n is 1 or 2.

4. Prostaglandin derivatives having the formula (XII)

wherein n is 1 or 2 and m is 0, 1 or 2.

5. Prostaglandin derivatives having the formula (XIII)

wherein n is 1 or 2.

6. Prostaglandin derivatives having the formula (XIV)

wherein n is 1 or 2 and m is 0, 1 or 2.

7. Prostaglandin derivatives having the formula (XV)

wherein R' is hydrogen atom, acetyl group, propionyl group or benzoyl group and n is 1 or 2 and m is 0, 1 or 2.

8. An abortifacient which comprises prostaglandin derivative according to claim 1 in combination with an inert pharmacologically acceptable carrier.

9. A parturifacient which comprises prostaglandin derivative according to claim 1 in combination with an inert pharmacologically acceptable carrier.

10. A contraceptive agent which comprises progstaglandin derivative according to claim 1 in combination with an inert pharmacologically acceptable carrier.

11. The composition of any of claims 8 to 10, wherein said prostaglandin is present in an amount greater than 0.0025% wt.